United States Patent [19]

Suzuki et al.

[11] 4,236,988
[45] Dec. 2, 1980

[54] APPARATUS FOR MEASURING ION ACTIVITIES

[75] Inventors: Nobuyoshi Suzuki, Hachiouji; Shigeru Yoshinari, Tokyo, both of Japan

[73] Assignee: Olympus Optical Co., Ltd., Tokyo, Japan

[21] Appl. No.: 15,440

[22] Filed: Feb. 26, 1979

[30] Foreign Application Priority Data

Mar. 10, 1978 [JP] Japan ................. 53-27462

[51] Int. Cl.³ .......................................... G01N 27/28
[52] U.S. Cl. .............................. 204/195 R; 204/1 T
[58] Field of Search .......... 204/195 R, 195 G, 195 M, 204/195 F, 195 B; 324/29, 30 R; 128/635; 364/416, 497; 422/62, 98

[56] References Cited

U.S. PATENT DOCUMENTS

| 3,467,591 | 9/1969 | Frant | 204/195 R |
| 3,484,359 | 12/1969 | Greene et al. | 204/195 R |
| 3,505,197 | 4/1970 | Malk et al. | 204/195 R |
| 3,892,652 | 7/1975 | Levine et al. | 204/195 R |

FOREIGN PATENT DOCUMENTS 42-3760 2/1967 Japan.

*Primary Examiner*—G. L. Kaplan
*Attorney, Agent, or Firm*—Darby & Cushman Cushman

[57] ABSTRACT

An apparatus for measuring ion activities comprising an electrode assembly, a sample cup, a mechanism for moving up and down said electrode assembly, a pipette for injecting a sample fluid and a system for injecting a reference solution, and so operating as to inject a sample fluid into said sample cup with the pipette for injecting sample fluid, move up and down said electrode assembly for assuring intimate contact between said electrode assembly and said sample fluid, measure ion activities in said sample fluid, inject a reference solution through said reference solution injecting system, wash said electrode assembly, discard the reference solution used for washing, inject the reference solution once again, measure ion activities in said reference solution and determine correct ion activities in said sample fluid on the basis of the levels of ion activities measured in said sample solution and those measured in said reference solution.

5 Claims, 4 Drawing Figures

APPARATUS FOR MEASURING ION ACTIVITIES

BACKGROUND OF THE INVENTION (a) Field of the Invention

The present invention relates to a method and an apparatus for measuring activities of ions which are chemically specific in physiological fluids.

(b) Description of the Prior Art

There has already been known the fact that, among ions in physiological fluids, ions of sodium (Na), potassium (K), etc. play important rolls. Na and K ions, for example, occupy high ratios of the cations contained in blood and are the most important for maintaining adequate osmotic pressure and equilibrium between acids and bases groups in blood. Further, measurements of ions in blood which is a typical cellular fluids are very important since they permit comprehending conditions such as water contents, metabolism of electrolytes as well as excitability of nerves and muscles. Furthermore, variations of ion concentration in physiological fluids are highly significant in clinical diagnosis of diseases such as diarrhea, dehydration, cardiac insufficiency, vomiting, etc. While various ions in physiological fluids are measured for the reasons described above, the flame photometry and atomic absorption photometry have chiefly been utilized conventionally for measuring Na and K ions which are of special importance. However, these have posed many problems related to preparations, operations and installation required for measuring apparatus therefor. Furthermore, these methods could not assure measuring accuracy high enough for the above-mentioned purpose since they do not measure activities but quantities of ions contained in samples.

As another method for measuring chemically specific ions in physiological fluids mentioned above, there is known a method to use electrodes which responds selectively to ions to be measured. This method using such electrodes for measuring ions in physiological fluids had, however, a defect that it involved large errors in measured results or remarkably degraded determination accuracy when the physiological fluids or electrodes were contaminated. Further, physiological fluids, especially blood, should preferably be collected in quantities as small as possible since collection of large quantities of physiological fluids will give serious influences on human bodies. Therefore, physiological fluids available for measurements are generally in very small quantities and contamination will affects measuring accuracy remarkably.

SUMMARY OF THE INVENTION

A general object of the present invention is to provide a method and an apparatus for measuring ion activities which are capable of measuring ion activities in very small quantities of physiological fluids without causing contamination of physiological fluids or electrodes and without deteriorating the tips of the electrodes. In order to measure ion activities by the method according to the present invention, a small quantity of sample fluid is put in a sample cup which is arranged in the vicinity of the electrodes and the electrodes are lowered down until the sample fluid is brought into contact with the electrodes. Then, the electrodes are moved up and down so as to assure close contact between the electrodes and sample fluid. In this condition, ion activities in the sample fluid are measured by the method already known to those skilled in the art. After the measurement, a low concentration reference solution which contains Na, K and Cl at the same ratios as those in the physiological fluid and is to be used for correcting measured values is poured into the sample cup, mixed with said physiological fluid and discarded. Further, the reference solution is poured into the sample cup and the electrodes are moved up and down for washing both the electrode tips and sample cup sufficiently. After washing, the reference solution is discarded. Then, the reference solution is poured into the sample cup for the third time and the electrodes are moved up and down to assure intimate contact between the solution are measured. On the basis of the ion activities in the reference solution thus measured, ion activities in the sample fluid are corrected to determine ion activities in the sample fluid. The reference solution is kept in the sample cup even after the measurement has completed. Immediately before proceeding to measurement of the next sample fluid, the reference solution is discarded from the sample cup and a new sample fluid is put into the sample cup. This sample is immediately measured through the processes already described above.

DESCRIPTION OF THE PREFERRED EMBODIMENTS

Figure 1:
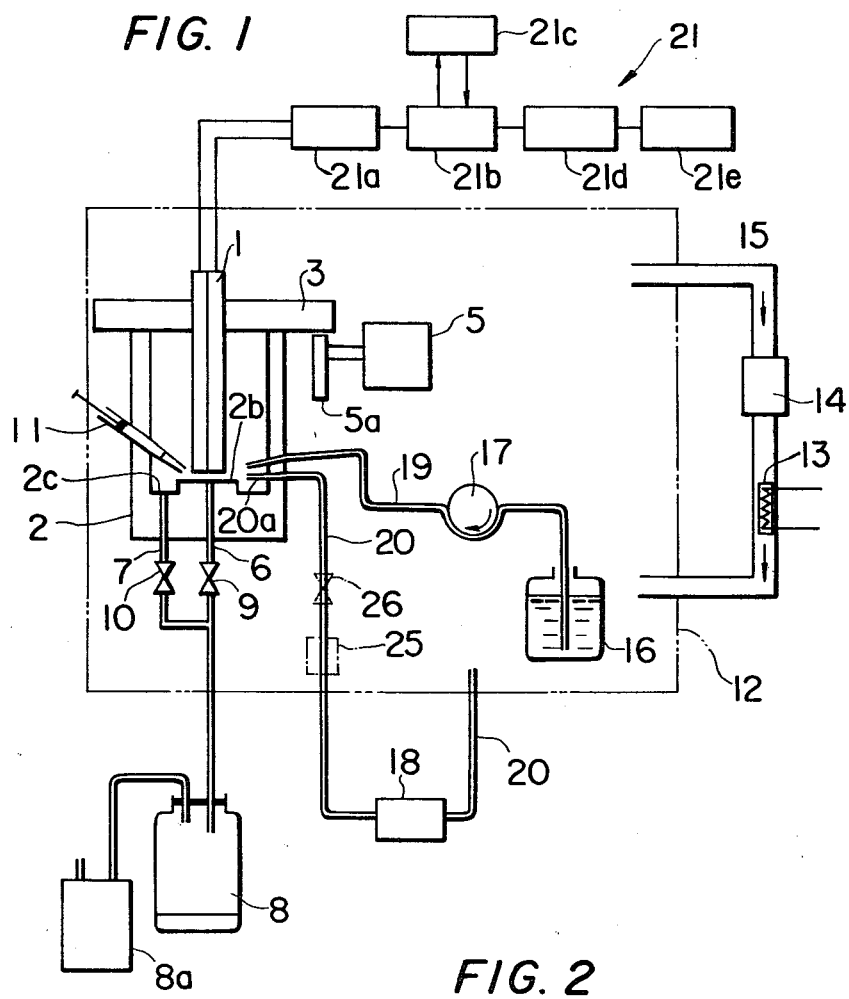
FIG. 1 shows a block diagram illustrating the construction of the apparatus for measuring ion activities by the method according to the present invention.
Figure 2:
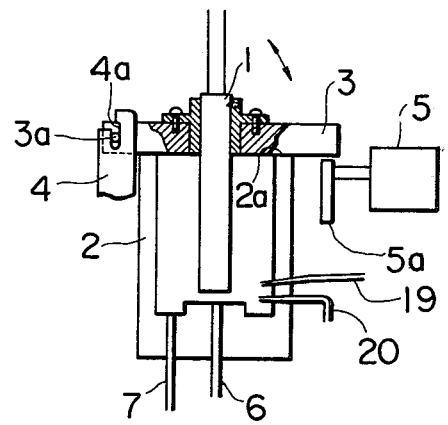
FIG. 2 through FIG. 4 show sectional views illustrating constructions of an electrode assembly to be used in the measuring apparatus according to the present invention.

Referring now to the accompanying drawings, the method according to the present invention and an embodiment of the apparatus to be used for measurement by said method will be described. In FIG. 1, the reference numeral 1 represents an electrode assembly which consists of electrodes for collecting ions of Na, K and Cl as well as a reference electrode. The reference numeral 2 designates a sample cup which is arranged in the vicinity of said electrode assembly 1 and the reference numeral 3 denotes a support which serves to hold the electrode assembly 1 and is mounted on an upper end surface 2a of the circumferential wall of the sample cup 2 as shown in FIG. 2. On one side of the support 3, a pin 3a is removably fitted into a slot 4a formed in a holder plate 4. On the other side of the support 3, there is arranged an eccentric disc 5a which is rotated by a motor 5, whereby the support 3 is moved up and down as indicated by an arrow in FIG. 2 and the electrode assembly 1 is also moved up and down accordingly. The reference numerals 6 and 7 represent tubes which are to be used for discarding liquid into a waste liquid bottle 8 while sucking the liquid from the sample cup by a drain pump 8a. The reference numerals 9 and 10 designate an electromagnetic valves which are attached in the courses of the tube 6 and 7 respectively. The reference numeral 11 denotes a pipette for injecting sample fluid, and the reference numeral 12 represents a thermostatted chamber (or oven) in which the electrode assembly, sample cup, etc. are arranged, and temperature is controlled at the constant level with a heater 13, a blower 14 and ventilating pipe 15. The reference numeral 16 designates a container for reference solution, the reference numeral 17 denotes a roller pump, the reference numeral 18 represents an air pump, the reference numerals 19 and 20 designate tubes respectively, and the reference numeral 21 denotes a measuring-recording apparatus which consists essentially of an amplifier 21a, a central processor unit (CPU) 21b, a memory 21c, a display unit 21d and a printer 21e. Now, operations of the above-described apparatus will be described in details. The sample cup 2 is filled with a reference solution in which the tip of the electrode assembly 1 is dipped. When a drain pushbutton switch (not shown in the drawings) is depressed, the drain pump 8a starts operating and opens the electromagnetic valve 9 so that the reference solution is discarded from the higher central portion 2b in the sample cup 2 through the tube 6, whereafter the drain pump 8a opens the electromagnetic valve 10 to discard the reference solution from the concave portion 2c in the sample cup. Though the valves 9 and 10 may be opened at the same time, it is preferable to open the valve 9 as early as possible in order to remove the reference solution as early as possible from the electrode assembly for permitting early commencement of measurement. In the next stage, the air pump starts operating to blow air from inside the oven 12 through the tip 20a of the tube 20 to the central portion of the sample cup 2. While the air is being blown as described above, the motor 5 operates to drive the electrode assembly to perform one and a half cycles of the vertical reciprocal motion. This motion is effective to remove the residual sample fluid used for the preceding measurement and adhering to the electrode assembly 1 and the sample cup 2, and also enhance the effects to clean the electrode tip and sample cup by displacing the portion blasted with the air. After the reference solution has been removed completely from the sample cup 2, the drain pump 8a and air pump 18 stop operating, and a ready lamp (not shown) comes on. At this stage, a sample fluid is injected to the central portion 2b in the sample cup 2 from the sample injection pipette 11.

When a major pushbutton switch is depressed, the motor 5 operates to lower the electrode assembly 1 down to the position shown in FIG. 2. Since the top end surface 2a of the circumferential wall of the sample cup is designed as a standard plane for locating the electrode assembly at its lower position, the tip of the electrode assembly is brought close to the central portion 2b of the sample cup 2 and into contact with the sample fluid injected therein. When the electrode assembly is moved up and down at the next stage, the sample fluid is brought into contact with the electrode assembly more uniformly between the sample cup 2 and electrode assembly 1. At this stage, the motor 5 stops operating and then the potential at each electrode element is measured by the electrode assembly and stored in the memory. After the measurements have been completed, the roller pump 17 operates to inject the reference solution into the sample cup 2 through the tube 19 for washing the electrode assembly. At the same time, the drain pump 8a operates to discard the reference solution from the sample cup 2. With a short time lag, the air pump 18 operates to clean the top surface of the central portion 2b of the sample cup 2 and lower surface of the electrode assembly 1. Then the drain pump 8a and air pump 18 stop operating, and the roller pump 17 starts operating again to inject the reference solution into the sample cup 2. After completing the injection of the reference solution, the electrode assembly is moved up and down by the operation of the motor 5 for further washing the electrode assembly 1 and sample cup 2, whereby the electrode assembly 1 and sample cup 2 are made free from contamination. Successively, the electromagnetic valves 9 and 10 are opened and the air pump 8a operates to remove the residual reference solution from the electrode assembly 1 and the central portion 2b of the sample cup 2. At this stage where the electrode assembly 1 and sample cup 2 have been completely cleaned as described above, the air pump 8a stops operating and electromagnetic valves 9 and 10 are closed. Then the roller pump 17 operates to pour the reference solution to the central portion 2a of the sample cup 2. After injection of the reference solution, the electrode assembly is moved up and down to assure intimate contact between the electrode tip and the reference solution. At this stage, potentials of Na, K and Cl in the reference solution are measured, and concentration of each type of ions in the sample fluid is determined on the basis of the measured value of the reference solution and that of the sample fluid which has already been measured and stored, whereby the analytical results are indicated on the display and printed out on the printer.

Figure 3:
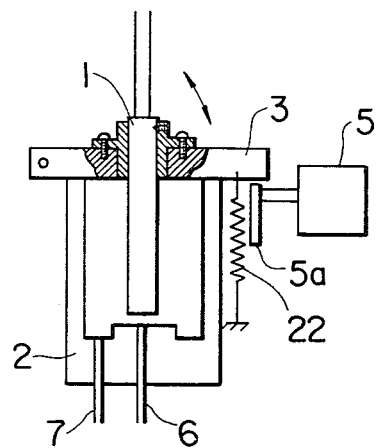
Figure 4:
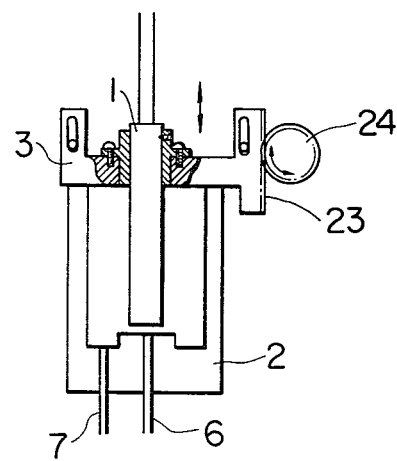

FIG. 3 and FIG. 4 illustrate different examples of mechanisms respectively for moving up and down the electrode assembly 1. In the mechanism shown in FIG. 3, the support 3 is forcibly pulled down by a spring 22 in contrast to the construction shown in FIG. 2 in which the support 3 is lowered down by its own weight. In the construction shown in FIG. 4, a rack 23 is formed on the side of the support 3 so that it is moved up and down by rotation of a pinion 24 which is in mesh with said rack.

In the apparatus for measuring ion activities according to the present invention, the cleaning effects can be enhanced by arranging an air tank 25 in the vicinity of the air pump 18 so that air can be compressed in said air tank and blown at a higher pressure while controlling opening and closing operation of the valve 26. Further, it will be possible not to use the single drain tube 6 but to arrange plural drain tubes under the Na and other electrodes respectively of the electrode assembly. Too large inside diameters of the tube tips will be unpreferable since they permit penetration of sample fluids, etc. into the tubes during sample injection and measurement.

As is easily understood from the foregoing descriptions, the method and apparatus for measuring ion activities according to the present invention can assure highly accurate measurements by lowering the electrode assembly to bring it into contact with small quantity of sample fluid at the measuring time and moving the electrode assembly up and down to provide intimate contact between the electrode assembly and the sample fluid. Furthermore, said method and apparatus do not cause degradation in sensitivity of the electrodes and permits commencing measurement quickly since the electrode assembly is dipped in the reference solution even after measurement has been completed. Moreover, the electrodes cannot be contaminated since the electrode assembly and sample cup are washed with the reference solution while moving up and down the electrode assembly. Cleaning can be performed without degrading sensitivity due to temperature drop in the vicinity of the electrode tip since internal air of the oven is blasted around the electrode tip for cleaning.

It is claimed:

1. An apparatus for measuring ion activities comprising an electrode assembly, a sample cup having a circumferential wall whose top surface is designed as a standard plane for properly positioning said electrode assembly, a support which serves for holding said electrode assembly and is arranged on the circumferential wall of said sample cup, a mechanism for moving up and down said electrode assembly by way of said support, a pipette for injecting a constant volume of sample fluid into said sample cup, a draining system for sucking liquid from said sample cup and discarding said liquid and a thermostatted chamber accommodating at least said electrode assembly, said sample cup and said sample injecting pipette, and so operating as to inject a sample fluid into said sample cup, lower said electrode assembly for bringing said sample fluid into contact with said electrode assembly, move up and down said electrode assembly for assuring intimate contact between said electrode assembly and said sample fluid, measure ion activities in said sample fluid, inject a reference solution into said sample cup after measurements of ion activities in said sample fluid, wash said electrode assembly and said sample cup with said reference solution, discard said reference solution, inject the reference solution once again and measure ion activities therein, and determine correct ion activities in said sample fluid on the basis of the ion activities measured in said sample fluid and those in said reference solution.

2. An apparatus for measuring ion activities according to claim 1 additionally comprising an air blower equipped with an air pump and a tube, said tube having one end arranged at a position near said electrode assembly and the other end arranged in said thermostatted chamber, said air pump being equipped to said tube, said air blower being arranged to dry said electrode assembly by blowing the air from the inside of said thermostatted chamber to said electrode assembly.

3. An apparatus for measuring ion activities according to claim 1 or 2 wherein one end of said support is rotatably supported and said electrode assembly is moved up and down by moving up and down the other end of said support with said mechanism for moving up and down said electrode assembly.

4. An apparatus for measuring ion activities according to claim 3 wherein the other end of said support is forcibly lowered under a force of a spring.

5. An apparatus for measuring ion activities according to claim 1 or 2 wherein said mechanism for moving up and down said electrode assembly consists of a rack formed on said support and a pinion in mesh with said rack.

* * * * *